(12) United States Patent
D'Armiento et al.

(10) Patent No.: US 8,846,757 B2
(45) Date of Patent: Sep. 30, 2014

(54) BIOACTIVE DEPSIDE AND ANTHOCYANIN COMPOUNDS, COMPOSITIONS, AND METHODS OF USE

(75) Inventors: Jeanine D'Armiento, New York, NY (US); Kurt Reynertson, New York, NY (US); Edward Kennelly, Bronx, NY (US); Alison Wallace, Vancouver (CA)

(73) Assignees: The Trustees of Columbia University in the City of New York, New York, NY (US); The Research Foundation of The City University of New York, New York, NY (US)

( * ) Notice: Subject to any disclaimer, the term of this patent is extended or adjusted under 35 U.S.C. 154(b) by 1492 days.

(21) Appl. No.: 12/309,804

(22) PCT Filed: Jul. 31, 2007

(86) PCT No.: PCT/US2007/017087
§ 371 (c)(1),
(2), (4) Date: Jan. 7, 2011

(87) PCT Pub. No.: WO2008/016593
PCT Pub. Date: Feb. 7, 2008

(65) Prior Publication Data
US 2011/0110885 A1    May 12, 2011

Related U.S. Application Data

(60) Provisional application No. 60/834,719, filed on Jul. 31, 2006.

(51) Int. Cl.
*A61K 31/235* (2006.01)
*A23L 1/30* (2006.01)
*A61K 31/7048* (2006.01)

(52) U.S. Cl.
CPC .......... *A61K 31/7048* (2013.01); *A23L 1/3002* (2013.01); *A61K 31/235* (2013.01); *Y10S 514/885* (2013.01)
USPC .......................................... 514/533; 514/885

(58) Field of Classification Search
None
See application file for complete search history.

(56) References Cited

U.S. PATENT DOCUMENTS 6,673,908 B1 * 1/2004 Stanton, Jr.

FOREIGN PATENT DOCUMENTS

WO    WO 02/09699    2/2002

OTHER PUBLICATIONS

Morton, J. Fruits of Warm Climates. Julia Morton: Winterville, NC, 1987; pp. 386-388.

Popenoe, W. "Fruits of the myrtle family," Manual of Tropical and Subtropical Fruits. Hafner Press: New York, 1920; pp. 272-311.
Giacometti, et al., "Subtropical myrtaceae," Neglected Crops: 1492 from a Different Perspective; Bermejo, J. E. H.; León, J., Eds.; FAO: Rome, 1994; pp. 229-237.
Einbond, et al., "Anthocyanin antioxidants from edible fruits," Food Chem. 2004, 84, 23-28.
Trevisan et al., "Carbohydrates, organic acids and anthocyanins," J. Food Sci. 1972, 37, 818-819.
Zanatta et al., "Determination of anthocyanins from camu-camu (*Myrciaria dubia*) by HPLC-PDA, HPLC-MS, and NMR," J. Agric. Food Chem. 2005, 53, 9531-9535.
Baggett; et al. "Bioactive benzophenones from garcinia xanthochymus fruits," J. Nat. Prod. 2005, 68, 354-360.
Ma et al., "Bioactive novel polyphenols from the fruit of manilkara zapota (sapodilla),"J. Nat. Prod. 2003, 66, 983-986.
Yang et al., "Antioxidant and cytotoxic isoprenylated coumarins from *Mammea americana*," Planta Med. 2005, 71, 852-860.
Yang et al., New bioactive polyphenols from *Theobroma grandiflorum* ("cupuacu"), J. Nat. Prod. 2003, 66, 1501-1504.
Ono et al., "Antioxidant ortho-benzolyloxyphenyl acetic acid ester, vaccihein A, from the fruit of rabbiteye blueberry," Chem. Pharm. Bull. 2002, 50, 1416-1417.

(Continued)

*Primary Examiner* — Savitha Rao
*Assistant Examiner* — Gregg Polansky
(74) *Attorney, Agent, or Firm* — Bryan Cave LLP

(57) ABSTRACT

Methods for modulating the level of a chemokine in a cell by administering to a cell an effective amount of a depside or an anthocyanin are provided. More particularly, a method for modulating the level of a chemokine in a cell by administering to a cell an effective amount of a depside having the structure of formula (IV): Formula (IV) wherein R is selected from H or $CH_3$ or an anthocyanin selected from cyanidin 3-glucoside, delphinidin 3-glucoside, or combinations thereof, or an enantiomer, optical isomer, diastereomer, N-oxide, crystalline form, hydrate, or pharmaceutically acceptable salt thereof is provided. Also provided are compounds according to Formulas I-IV, pharmaceutical compositions, unit dosage forms, and food or feed supplements containing such compounds. Methods for treating a condition in a mammal and for treating or ameliorating a condition, such as for example, chronic obstructive pulmonary disease (COPD) by administering an effective amount of a composition containing such compounds are also provided. Further provided is an extract obtained from the fruit of *Myrciaria cauliflora* containing at least one compound of the present invention in substantially pure form.

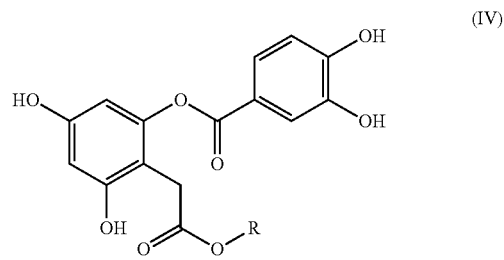

(IV)

7 Claims, No Drawings

(56) References Cited

OTHER PUBLICATIONS

Zgorka et al., "Variation of free phenolic acids in medicinal plants belonging to the lamiaceae family," J. Pharm. Biomed. Anal. 2001, 26, 79-87.

Choi, et al. "Deoxypodophyllotoxin reduces skin pigmentation of brown guinea pigs," Planta Med. 2004, 70, 378-380.

Kumar et al, "Lichen metabolites Antiproliferative and cytotoxic activity of gyrophoric, usnic, and diffractaic acid on human keratinocyte growth," J. Nat. Prod. 1999, 62, 821.

Neamati et al., "Depsides and depsidones as inhibitors of HIV-1 integrase: discovery of novel inhbitiors through 3D database searching," J. Med. Chem. 1997, 40, 942-951.

Nielsen et al, "Fungal depside, guisinol, from a marine derived strain of Emericella unguis," Phytochemistry. 1998, 50, 263-265.

Gerrard et al, "Structure of the active site of prostaglandin synthase from studies of depsides: an alternate view," Prostaglandins Leukot. Med. 1984, 13, 139-142.

Sankawa et al., "Depside as potent inhibitor of prostaglandin biosynthesis: a new active site model for fatty acid cyclooxygenase," Prostaglandins. 1982, 24, 21-33.

Kumar et al, "Lichen metabolites. 1. Inhibitory action against leukotriene B4 biosynthesis by a non-redox mechanism," J. Nat. Prod. 1999, 62, 817-820.

Kumar KC, S et al., "Depsides as non-redox inhibitors of leukotriene B4 biosynthesis and HaCaT cell growth, Novel." Eur. J. Med. Chem. 2000, 35, 405-411.

Agrawal et al., "Flavonoid Glycosides," Carbon-13 NMR of Flavonoids, Elsevier: New York, 1989; vol. 39, pp. 283-364.

Lu et al., "Novel pyranoanthocyanins from black currant seed," Tetrahedron Lett. 2000, 41, 5975-5978.

Seeram et al, "Identification of phenolic compounds in strawberries by liquid chromatography electrospray ionization mass spectroscopy," Food Chem. 2006, 97, 1-11.

Ikuta, H. et al., "NMR Spectra of cyanidin and chrysanthemin," Heterocycles. 1985, 23, 121-126.

Miyazawa et al., "Tyrosinase inhibitor from black rice bran," J. Agric. Food Chem. 2003, 51, 6953-6956.

Sang, S. et al., "Antioxidative phenolic compounds isolated from almond skins (Prunus amygdalus batsch)," J. Agric. Food Chem. 2002, 50, 2459-2463.

de Boer, "Cytokines and therapy in COPD," W. I. Chest. 2002, 121, 209S-218S.

Barnes, "Potential novel therapies for chronic obstructive pulmonary disease," In Chronic Obstructive Pulmonary Disease: Pathogenesis to Treatment, Wiley & Sons: 2001; 255-272.

Koefler et al, "Role of cytolines in cardiovascular diseases: a focus on endothelial responses to inflammation," Clin. Sci. 2005, 108, 205-213.

Biswas et al., "Curcumin induces glutathione biosynthesis and inhibits NF-κB activation and interleukin-8 release in alveolar.."Antioxid. Redox Signal. 2005, 7, 32-41.

Shimizu et al., "(−)-Epigallocatechin gallate and polyphenon E inhibit growth and activation of the epidermal growth factor receptor . . . " Clin. Cancer Res. 2005, 11, 2735-27.

Marko et al., "The substitution pattern of anthocyanidins affects different cellular signaling cascades regulating . . . " Mol. Nutr. & Food Res. 2004, 48, 318-325.

Meiers et al., "The anthocyanidins cyanidin and delphinidin are potent inhibitors of the epidermal growth-factor receptor," J. Agric. Food Chem. 2001, 49, 958-962.

Kong et al., "Analysis and biological activities of anthocyanins," Phytochemistry. 2003, 64, 923-933.

Cimino et al., "Effect of cyanidin-3-O-glucoside on UVB-Induced response in human keratinocytes," J. Agric. Food Chem. 2006, 54, 4041-4047.

Luo et al, "Polyphenolic antioxidants from the fruits of chrysophyllum cainito (star apple)," J. Agric. Food Chem. 2002, 50, 1379-1382.

Laurent et al., "Cigarette smoke blocks cross-linking of elastin in vitro," Am. Rev. Respir. Dis. 1983, 127, 189-192.

Shimizu et al., "Effects of acyclic retinoid on growth, cell cycle control, epidermal growth factor receptor . . . " Clin. Can. Res. 2004, 10, 1130-1140.

Kuisle O. et al., J. Org Chem., 64(22): 8063-8075 (1999).

Kuisle O, et al. Tetrahedrom Letters, 40(6):1203-1206 (1999).

Sidwell, R.W. et al. Chemotherapy, 40(1):42-50 (1994).

Ono et al. "Antioxidant Ortho-Benzoyloxyphenyl Acetic Acid Ester, Vacciheim A, from the Fruit of Rabbiteye . . . " Chem. Pharm. Bull. (2002) vol. 50. No. 10, pp. 1416-1417.

Hillenbrand et al. "Depsides from the Petal of *Papaver rhoeas*" Planta Medica (2004) vol. 70 pp. 380-382.

\* cited by examiner

BIOACTIVE DEPSIDE AND ANTHOCYANIN COMPOUNDS, COMPOSITIONS, AND METHODS OF USE

CROSS-REFERENCE TO RELATED APPLICATIONS

This application is the National Stage of International Application No. PCT/US2007/017087, filed Jul. 31, 2007, which claims the benefit of U.S. Provisional Patent Application Ser. No. 60/834,719, filed Jul. 31, 2006, the entire disclosure of which is relied upon and incorporated by reference herein.

FIELD OF THE INVENTION

The present invention relates to compounds, compositions, and methods for modulating the level of a chemokine in a cell by administering to a cell an effective amount of a depside, an anthocyanin, or combinations thereof. More particularly, the present invention relates to methods for using the compounds and compositions disclosed herein to treat or ameliorate a condition in a mammal, such as for example, chronic obstructive pulmonary disease (COPD).

BACKGROUND OF THE INVENTION

The *jaboticaba* (*Myrciaria cauliflora* (Mart.) O.Berg. (Myrtaceae)) is a small tree native to the Minas Gerais region near Rio de Janeiro in southern Brazil grown for the purple, grape-like fruits it produces. Traditionally, an astringent decoction of the sun-dried skins has been used as a treatment for hemoptysis, asthma, diarrhea, and gargled for chronic inflammation of the tonsils (1). The fruit is 3-4 cm in diameter with one to four large seeds, borne directly on the main trunks and branches of the plant, lending a distinctive appearance to the fruiting tree. The *jaboticaba* fruit has a thick, purple, astringent skin that covers a sweet, white, gelatinous flesh. Common in Brazilian markets, *jaboticabas* are largely eaten fresh. *Jaboticaba*'s popularity has been likened to that of grapes in the US (2). The fresh fruit may begin to ferment 3 to 4 days after harvest, so it is often used to make jams, tarts, strong wines, and liqueurs.

In Brazil, the fruit of several species, namely *M. jaboticaba* (Vell.) O.Berg, *M. tenella* (DC.) O.Berg, and *M. trunciflora* O.Berg, share the same common name (1-3). The phytochemistry of these fruits has not been extensively reported in the literature. The *jaboticaba* (no species distinguished) has been reported to contain tannins (1). The presence of cyanidin 3-glucoside (Compound 3) in *M. cauliflora* has been reported (4). *M. jaboticaba* reportedly contains peonidin 3-glucoside and its aglycone (5), and the related camu-camu berry (*M. dubia*), an edible fruit known for its high levels of ascorbic acid, contains Compound 3 and delphinidin 3-glucoside (Compound 4) as its main pigments (6).

Depsides are phenolic compounds composed of two or more monocyclic aromatic units linked by an ester bond. They are most often found in lichens, but have also been isolated from higher plants, including species of the Ericaceae, Lamiaceae, and Papaveraceae (10, 11). They have not been previously reported in the Myrtaceae. Depsides have antibiotic, anti-HIV, and antiproliferative activity (12, 13). Depsides also act as inhibitors of prostaglandin biosynthesis and leukotriene $B_4$ biosynthesis. Depsides are also potent non-steroidal anti-inflammatories (14).

The anthocyanins are a group of well-studied phenolic compounds with antioxidant, anti-inflammatory, antimutagenic, and cancer chemopreventative activities (21). In one study, it was shown that UVB-exposed HaCaT keratinocytes pretreated with Compound 3 were protected from UVB-induced inflammation, inhibiting NF-kB and AP-1 activation and IL-8 mRNA expression (22). Depsides from foods and botanicals are less well-studied than the anthocyanins, possibly as a result of their limited distribution in higher plants, and their ability to inhibit IL-8 production and cytotoxcity against colon cancer cells has not previously been reported.

The *jaboticaba* is rich in anthocyanins, phenolic acids, flavonoids, and contains depsides. Accordingly, it would be advantageous to provide, isolate, and characterize the active compound(s) responsible for the strong antiradical activity of the crude methanolic extracts of the *jaboticaba*. It would also be advantageous to provide bio-active compositions containing these bio-active compounds and methods of administering them.

SUMMARY OF THE INVENTION

One embodiment of the present invention is method for modulating the level of a chemokine in a cell. This method comprises administering to a cell an effective amount of a depside, anthocyanin, or a combination thereof, which is sufficient to modulate the level of a chemokine in a cell.

Another embodiment of the present invention is a pharmaceutical composition for treating a condition in a mammal. This method comprises administering to the mammal a pharmaceutically acceptable carrier and a compound having the structure of formula (IV):

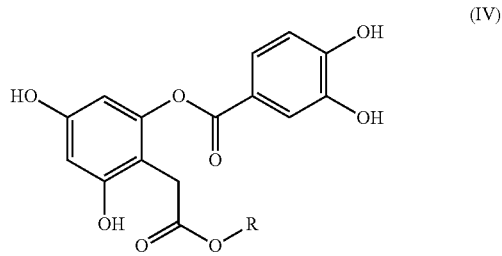

wherein R is selected from H or $CH_3$ or a compound selected from cyanidin 3-glucoside, delphinidin 3-glucoside, or combinations thereof, or an enantiomer, optical isomer, diastereomer, N-oxide, crystalline form, hydrate, or pharmaceutically acceptable salt thereof.

An additional embodiment of the present invention is a method for treating a condition in a mammal. This method comprises administering to the mammal an effective amount of a pharmaceutically acceptable carrier and a pharmaceutically acceptable composition comprising a compound having the structure of formula (IV):

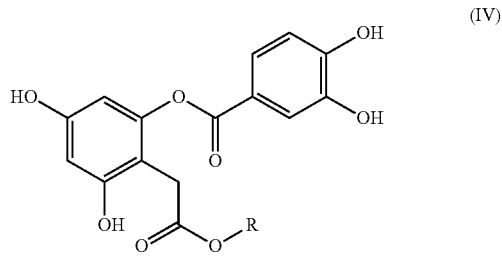

wherein R is selected from H or CH₃ or a compound selected from cyanidin 3-glucoside, delphinidin 3-glucoside, or combinations thereof, or an enantiomer, optical isomer, diastereomer, N-oxide, crystalline form, hydrate, or pharmaceutically acceptable salt thereof.

Another embodiment of the present invention is a method for treating or ameliorating chronic obstructive pulmonary disease (COPD). This method comprises administering to a mammal an effective amount of a composition comprising a pharmaceutically acceptable carrier and a compound having the structure of formula (IV):

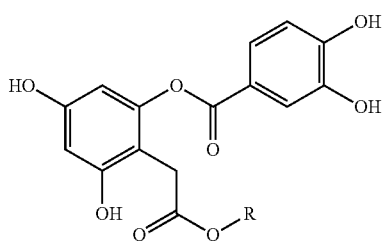

(IV)

wherein R is selected from H or CH₃ or a compound selected from cyanidin 3-glucoside, delphinidin 3-glucoside, or combinations thereof, or an enantiomer, optical isomer, diastereomer, N-oxide, crystalline form, hydrate, or pharmaceutically acceptable salt thereof.

A further embodiment of the present invention is a unit dosage form comprising a pharmaceutically acceptable carrier and a compound having the structure of formula (IV):

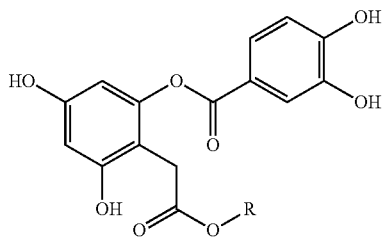

(IV)

wherein R is selected from H or CH₃ or a compound selected from cyanidin 3-glucoside, delphinidin 3-glucoside, or combinations thereof, or an enantiomer, optical isomer, diastereomer, N-oxide, crystalline form, hydrate, or pharmaceutically acceptable salt thereof.

An additional embodiment of the present invention is a food or feed supplement comprising an acceptable carrier and a compound having formula (IV):

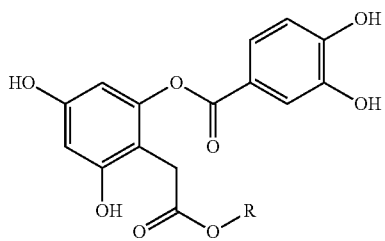

(IV)

wherein R is selected from H or CH₃ or a compound selected from cyanidin 3-glucoside, delphinidin 3-glucoside, or combinations thereof, or an enantiomer, optical isomer, diastereomer, N-oxide, crystalline form, hydrate, or pharmaceutically acceptable salt thereof.

Another embodiment of the present invention is an extract obtained from the fruit of *Myrciaria cauliflora* comprising, in substantially pure form, a compound having formula (IV):

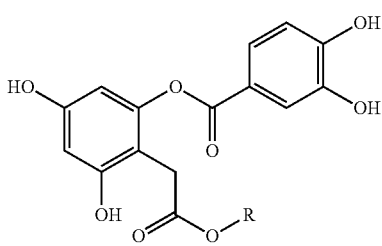

(IV)

wherein R is selected from H or CH₃ or a compound selected from cyanidin 3-glucoside, delphinidin 3-glucoside, or combinations thereof.

A further embodiment of the present invention is a compound of formula (I):

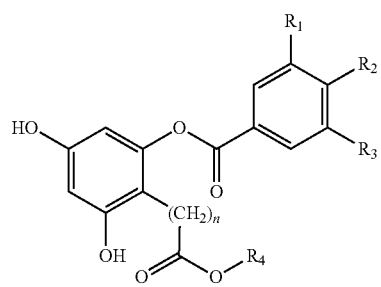

(I)

wherein $R_1$, $R_2$, and $R_3$ are independently selected from H, hydroxy, $C_{1-8}$alkyl, $C_{1-8}$alkoxy, $C_{1-8}$aralkyl, 3- to 8-membered carbocyclic, 3- to 8-membered heterocyclic, 3- to 8-membered aryl, or 3- to 8-membered heteroaryl, acyl, alkylsulfonyl, and arylsulfonyl, wherein each alkyl, alkoxy, aralkyl, carbocyclic, heterocyclic, aryl, heteroaryl, acyl, alkylsulfonyl, and arylsulfonyl is optionally substituted with at least one substituent;

$R_4$ is selected from H, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, carboxylate, ester, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether, wherein each alkyl, alkoxy, carbocyclic, heterocyclic, aryl, heteroaryl, carboxylate, ester, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether is optionally substituted with at least one substituent;

$R^7$ is selected from H, $C_{1-8}$alkyl, carbocycle, aryl, heteroaryl, heterocycle, alkylaryl, alkylheteroaryl, and alkylheterocycle, wherein each alkyl, carbocycle, aryl, heteroaryl, heterocycle, alkylaryl, alkylheteroaryl, and alkylheterocycle may be optionally substituted with at least one substituent;

$R^8$ is selected from H, $C_{1-8}$alkyl, $C_{1-8}$alkenyl, $C_{1-8}$alkynyl, aryl, carbocycle, heteroaryl heterocycle, alkylaryl, alkylheteroaryl, alkylheterocycle, and heteroaromatic, wherein each alkyl, alkenyl, alkynyl, aryl, carbocycle, heteroaryl, heterocycle, alkylaryl, alkylheteroaryl, alkylheterocycle, and heteroaromatic may be optionally substituted with at least one substituent;

and n is from 1 to 5, with the proviso that $R_1$ and $R_4$ cannot both be H and that when $R_1$ is $OCH_3$, $R_4$ cannot be $CH_3$; or an enantiomer, optical isomer, diastereomer, N-oxide, crystalline form, hydrate, or pharmaceutically acceptable salt thereof.

An additional embodiment of the present invention is a compound of formula (II):

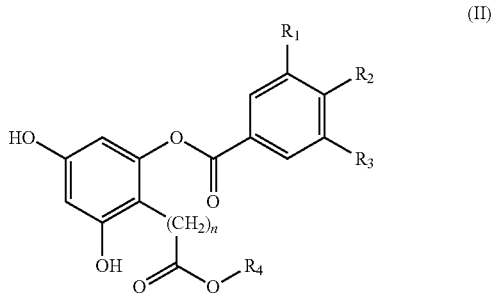

(II)

wherein $R_1$, $R_2$, and $R_3$ are independently selected from H, hydroxy, $C_{1-3}$alkyl, and $C_{1-3}$alkoxy, wherein each alkyl and alkoxy is optionally substituted with at least one substituent;

$R_4$ is selected from H, $C_{1-3}$alkyl, and $C_{1-3}$alkoxy wherein each alkyl and alkoxy, is optionally substituted with at least one substituent;

$R^7$ is selected from H, $C_{1-8}$alkyl, carbocycle, aryl, heteroaryl, heterocycle, alkylaryl, alkylheteroaryl, and alkylheterocycle, wherein each alkyl, carbocycle, aryl, heteroaryl, heterocycle, alkylaryl, alkylheteroaryl, and alkylheterocycle may be optionally substituted with at least one substituent;

$R^8$ is selected from H, $C_{1-8}$alkyl, $C_{1-8}$alkenyl, $C_{1-8}$alkynyl, aryl, carbocycle, heteroaryl, heterocycle, alkylaryl, alkylheteroaryl, alkylheterocycle, and heteroaromatic, wherein each alkyl, alkenyl, alkynyl, aryl, carbocycle, heteroaryl, heterocycle, alkylaryl, alkylheteroaryl, alkylheterocycle, and heteroaromatic may be optionally substituted with at least one substituent;

and n is from 1 to 5, with the proviso that $R_1$ and $R_4$ cannot both be H and that when $R_1$ is $OCH_3$, $R_4$ cannot be $CH_3$; or an enantiomer, optical isomer, diastereomer, N-oxide, crystalline form, hydrate, or pharmaceutically acceptable salt thereof.

Another embodiment of the present invention is a compound of formula (III):

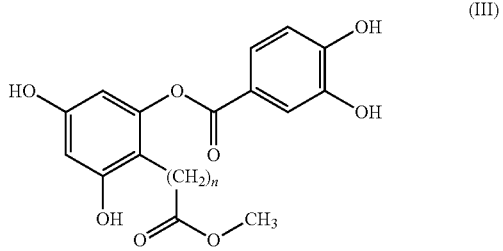

(III)

wherein n is 1-5. Preferably, n is 1.

A further embodiment of the present invention is a compound of the formula:

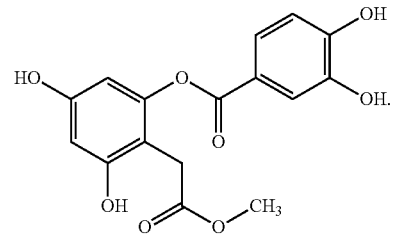 [SMILES: COC(=O)Cc1c(O)cc(O)cc1OC(=O)c1ccc(O)c(O)c1]

DETAILED DESCRIPTION OF THE INVENTION

The study of antioxidants and cancer chemopreventative compounds from tropical fruits is ongoing (7-9). Crude methanolic extracts of the *jaboticaba* have strong antiradical activity in the 1,1-diphenyl-2-picrylhydrazyl (DPPH) assay ($IC_{50}$=35 μg/mL). A new depside, jaboticabin (Compound 1), was isolated from the crude methanolic extracts of *jaboticaba*. In addition, the related depside 2-O-(3,4-dihydroxybenzoyl)-2,4,6-trihydroxyphenylacetic acid (Compound 2), delphinidin 3-glucoside (Compound 4), pyranocyanin B, quercetin, isoquercitrin, quercimeritrin, quercitrin, rutin, myricitrin, cinnamic acid, O-coumaric acid, gallic acid, protocatechuic acid, methyl protocatechuate, and ellagic acid were identified in this species for the first time.

The structures of Compounds 1 and 2 are shown below:

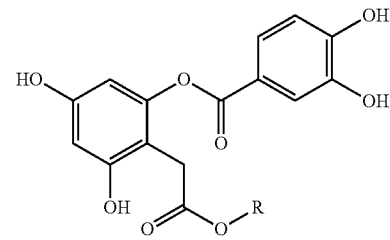

wherein R is $CH_3$ (Compound 1) or H (Compound 2).

Compounds 1 and 2 (depsides), exhibit antiradical activity in the DPPH assay, colon cancer cell cytotoxicity, and significantly inhibit chemokine interleukin (IL)-8 production in human small airway epithelial (SAE) cells before and after treatment with cigarette smoke extract (CSE). Compounds 3 and 4 (anthocyanins), major constituents of *jaboticaba* fruits, also display significant activity against IL-8 production in SAE cells. Compounds 1-4 were more effective at blocking IL-8 production in untreated SAE cells than catechin. Compounds 2 and 4 were more effective than catechin at blocking cigarette smoke-induced inflammation. Thus, *jaboticaba* anthocyanins and depsides exhibit good antiradical activity, cytotoxicity, and inhibit IL-8 production in both untreated SAE cells and those treated with proinflammatory CSE. (See Examples, below.)

IL-8 is a chemokine implicated in some cancers and a wide range of chronic inflammatory conditions, including rheumatoid arthritis, and heart and lung diseases (12, 16, 17). The ability of Compounds 1 and 2 to reduce IL-8 production suggests that they have an important anti-inflammatory action.

Chronic obstructive pulmonary disease (COPD) is a complex lung disease characterized by irreversible airflow obstruction due to chronic inflammation. COPD includes chronic obstructive bronchiolitis (fibrosis and obstruction of small airways) and emphysema (permanent enlargement of the airspaces distal to the terminal bronchioles accompanied by destruction of lung parenchyma). COPD is considered steroid-resistant, and it has been noted that non-steroidal anti-inflammatories that target chemokine pathways are needed as new therapies (16, 18). The ability of *jaboticaba* depsides and anthocyanins, e.g., Compounds 1-4, to reduce inflammation secondary to smoke exposure means these compound have promise as novel therapies for COPD.

Moreover, the cytotoxicity of Compounds 1, 2, and 4 is comparable to $IC_{50}$ values for 5-fluorouracil (5-FU), a drug used to treat colon cancer, epigallocatechin gallate (EGCG), and Polyphenon E (Poly E), a standardized decaffeinated green tea extract (8, 19). Thus, these compounds show promise as treatments for colon cancer.

Accordingly, one embodiment of the present invention is a method for modulating the level of a chemokine in a cell. This method includes administering to a cell an effective amount of a depside or anthocyanin, which is sufficient to modulate the level of a chemokine in a cell.

As used herein, the term "depside" means a phenolic compound composed of two or more monocyclic aromatic units linked by an ester bond. As used herein, the term "chemokine" means one of a family of pro-inflammatory activation-inducible cytokines, or small protein signals secreted by cells. Chemokines may induce directed chemotaxis in nearby responsive cells, hence the name chemotactic cytokines. Preferably, the chemokine is IL-8.

As used herein the term "anthocyanin" means a water soluble flavonoid pigment that reflects light in the red to blue range of the visible spectrum, depending on the pH of the surrounding solution. Anthocyanins are found exclusively in the plant kingdom, and have been observed to occur in all tissues of higher plants. Preferably, the anthocyanin is cyanidin 3-glucoside, delphinidin 3-glucoside, or combinations thereof, or an enantiomer, optical isomer, diastereomer, N-oxide, crystalline form, hydrate, or pharmaceutically acceptable salt thereof.

As used herein, the term "modulate" means to increase or decrease the amount of, e.g., a chemokine, in a cell as compared to the level of, e.g., the chemokine, in an untreated cell. Preferably, modulate means to decrease the level of the chemokine in the cell.

The present invention also includes compounds of formula (I):

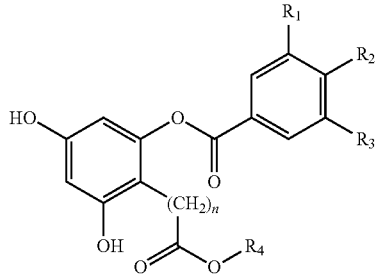

(I)

wherein
$R_1$, $R_2$, and $R_3$ are independently selected from H, hydroxy, $C_{1-8}$alkyl, $C_{1-8}$alkoxy, $C_{1-8}$aralkyl, 3- to 8-membered carbocyclic, 3- to 8-membered heterocyclic, 3- to 8-membered aryl, or 3- to 8-membered heteroaryl, acyl, alkylsulfonyl, and arylsulfonyl, wherein each alkyl, alkoxy, aralkyl, carbocyclic, heterocyclic, aryl, heteroaryl, acyl, alkylsulfonyl, and arylsulfonyl is optionally substituted with at least one substituent;

$R_4$ is selected from H, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, carboxylate, ester, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether, wherein each alkyl, alkoxy, carbocyclic, heterocyclic, aryl, heteroaryl, carboxylate, ester, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether is optionally substituted with at least one substituent;

$R^7$ is selected from H, $C_{1-8}$alkyl, carbocycle, aryl, heteroaryl, heterocycle, alkylaryl, alkylheteroaryl, and alkylheterocycle, wherein each alkyl, carbocycle, aryl, heteroaryl, heterocycle, alkylaryl, alkylheteroaryl, and alkylheterocycle may be optionally substituted with at least one substituent;

$R^8$ is selected from H, $C_{1-8}$alkyl, $C_{1-8}$alkenyl, $C_{1-8}$alkynyl, aryl, carbocycle, heteroaryl, heterocycle, alkylaryl, alkylheteroaryl, alkylheterocycle, and heteroaromatic, wherein each alkyl, alkenyl, alkynyl, aryl, carbocycle, heteroaryl, heterocycle, alkylaryl, alkylheteroaryl, alkylheterocycle, and heteroaromatic may be optionally substituted with at least one substituent;

and n is from 1 to 5, with the proviso that $R_1$ and $R_4$ cannot both be H and that when $R_1$ is $OCH_3$, $R_4$ cannot be $CH_3$; or an enantiomer, optical isomer, diastereomer, N-oxide, crystalline form, hydrate, or pharmaceutically acceptable salt thereof.

In the present invention, each optional substituent is independently selected from the group consisting of H, cyano, oxo, nitro, acyl, acylamino, halogen, hydroxy, amino acid, amine, amide, carbamate, ester, ether, $C_{1-8}$alkanoic acid, carboxylic acid, thio, thioalkyl, thioester, thioether, $C_{1-8}$ alkyl, $C_{1-8}$alkoxy, $C_{1-8}$alkenyl, $C_{1-8}$aralkyl, 3- to 8-membered carbocyclic, 3- to 8-membered heterocyclic, 3- to 8-membered aryl, or 3- to 8-membered heteroaryl, sulfate, sulfonamide, sulfoxide, sulfonate, sulfone, alkylsulfonyl, and arylsulfonyl.

In another embodiment, the present invention includes compounds of formula (II):

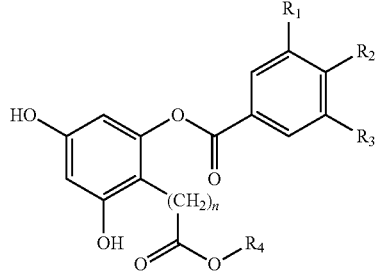

(II)

wherein
R₁, R₂, and R₃ are independently selected from H, hydroxy, $C_{1-3}$alkyl, and $C_{1-3}$alkoxy, wherein each alkyl and alkoxy is optionally substituted with at least one substituent;
R₄ is selected from H, $C_{1-3}$alkyl, and $C_{1-3}$alkoxy wherein each alkyl and alkoxy, is optionally substituted with at least one substituent;
$R^7$ is selected from H, $C_{1-8}$alkyl, carbocycle, aryl, heteroaryl, heterocycle, alkylaryl, alkylheteroaryl, and alkylheterocycle, wherein each alkyl, carbocycle, aryl, heteroaryl, heterocycle, alkylaryl, alkylheteroaryl, and alkylheterocycle may be optionally substituted with at least one substituent;
$R^8$ is selected from H, $C_{1-8}$alkyl, $C_{1-8}$alkenyl, $C_{1-8}$alkynyl, aryl, carbocycle, heteroaryl, heterocycle, alkylaryl, alkylheteroaryl, alkylheterocycle, and heteroaromatic, wherein each alkyl, alkenyl, alkynyl, aryl, carbocycle, heteroaryl, heterocycle, alkylaryl, alkylheteroaryl, alkylheterocycle, and heteroaromatic may be optionally substituted with at least one substituent;
and n is from 1 to 5,
with the proviso that R₁ and R₄ cannot both be H and that when R₁ is OCH₃, R₄ cannot be CH₃; or an enantiomer, optical isomer, diastereomer, N-oxide, crystalline form, hydrate, or pharmaceutically acceptable salt thereof.

In a further embodiment, the present invention includes compounds of formula (III):

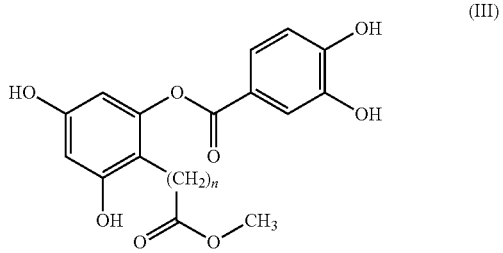

(III)

wherein n is 1-5. Preferably, n is 1.

In another embodiment, the present invention includes compounds of formula (IV):

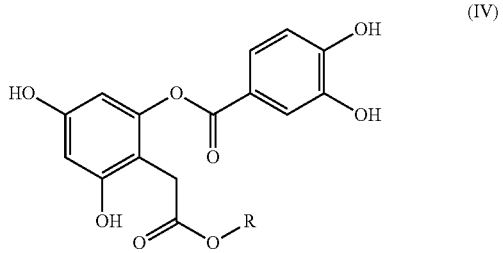

(IV)

wherein R is selected from H or CH₃ an anthocyanin, combinations thereof, or an enantiomer, optical isomer, diastereomer, N-oxide, crystalline form, hydrate, or pharmaceutically acceptable salt thereof, which is sufficient to modulate the level of a chemokine in a cell. Preferably, R is CH₃.

As used herein, the term "acyl" has its art-recognized meaning and refers to a group represented by the general formula hydrocarbylC(O)—, preferably alkylC(O)—.

As used herein, the term "acylamino" has its art-recognized meaning and refers to an amino group substituted with an acyl group and may be represented, for example, by the formula hydrocarbylC(O)NH—.

As used herein, the term "acyloxy" has its art-recognized meaning and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer, such as from 1 to 8. Likewise, preferred cycloalkyls have from 3-10 carbon atoms in their ring structure, and more preferably have 5, 6 or 7 carbons in the ring structure.

Moreover, unless otherwise indicated, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF₃, —CN and the like. Exemplary substituted alkyls are described below. Cycloalkyls can be further substituted with alkyls, alkenyls, alkoxys, alkylthios, aminoalkyls, carbonyl-substituted alkyls, —CF₃, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

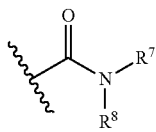

wherein $R^7$ and $R^8$ each independently represent a hydrogen or hydrocarbyl group, or $R^7$ and $R^8$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

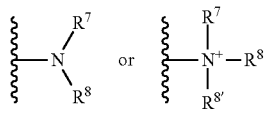

wherein $R^7$, $R^8$, and $R^{8'}$ each independently represent a hydrogen or a hydrocarbyl group, or $R^7$ and $R^8$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 3- to 8-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

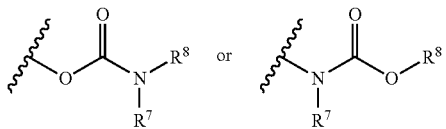

wherein $R^7$ and $R^8$ independently represent hydrogen or a hydrocarbyl group.

The terms "carbocycle", "carbocyclyl", and "carbocyclic", as used herein, refers to a non-aromatic saturated or unsaturated ring in which each atom of the ring is carbon. Preferably a carbocycle ring contains from 3 to 10 atoms, more preferably from 3 to 8 atoms, including 5 to 7 atoms, such as for example, 6 atoms.

The term "carboxy", as used herein, refers to a group represented by the formula —$CO_2H$.

The term "ester", as used herein, refers to a group —C(O)$OR^7$ wherein $R^7$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" are used interchangeably herein and mean halogen and include chloro, fluoro, bromo, and iodo.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 3- to 8-membered rings, more preferably 5- to 7-membered rings, even more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 8-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term lower when used in conjunction with a chemical moiety, such as, acyl, acyloxy, alkyl, alkenyl, alkynyl, or alkoxy is meant to include groups where there are ten or fewer non-hydrogen atoms in the substituent, preferably eight or fewer, such as for example, from about 3 to 8 carbon atoms, more preferably less than 6 carbon atoms. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 3 to 8, such as for example, 5 to 7.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

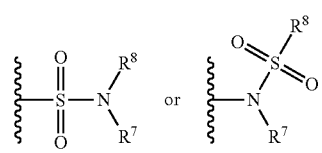

wherein $R^7$ and $R^8$ independently represents hydrogen or hydrocarbyl.

The term "sulfoxide" is art-recognized and refers to the group —S(O)—$R^7$, wherein $R^7$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—$R^7$, wherein $R^7$ represents a hydrocarbyl.

The term "thioalkyl", as used herein, refers to an alkyl group substituted with a thiol group.

The term "thioester", as used herein, refers to a group —C(O)S$R^7$ or —SC(O)$R^7$ wherein $R^7$ represents a hydrocarbyl.

The term "thioether", as used herein, is equivalent to an ether, wherein the oxygen is replaced with a sulfur.

In the present invention, the compounds of the present invention may be isolated from natural sources, such as, e.g., in the case of Compounds 1 and 2 from the *jaboticaba*. Alternatively, Compound 2 may be isolated from, e.g., the dried petals of *P rhoeas* L. See, e.g., Hillenbrand M. et al., Planta Med, 70:378-380 (2004). Alternatively, any of the compounds within the scope of formulae I-III may be synthesized using routine skill in the art. See, e.g., Kuisle O. et al., J Org Chem., 64(22):8063-8075 (1999) and Kuisle O. et al., Tetrahedron Letters, 40(6):1203-1206 (1999).

The present invention also includes compositions, including pharmaceutical compositions, containing any of the foregoing compounds. The present invention further includes methods of treating or ameliorating a condition as defined below, particularly COPD, by administering to a mammal an effective amount of any of the foregoing compounds or compositions.

A further embodiment of the present invention is a pharmaceutical composition for treating a condition in a mammal. In this embodiment, the composition contains a pharmaceutically acceptable carrier and a compound having the structure of formula (IV):

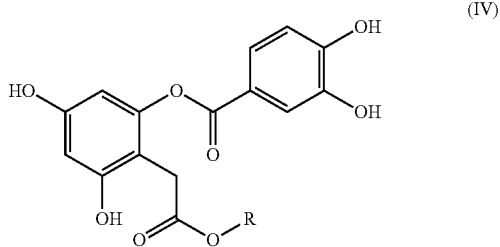

wherein R is selected from H or CH$_3$ or a compound selected from cyanidin 3-glucoside, delphinidin 3-glucoside, or combinations thereof, or an enantiomer, optical isomer, diastereomer, N-oxide, crystalline form, hydrate, or pharmaceutically acceptable salt thereof. Preferably, R is CH$_3$.

An additional embodiment of the present invention is a method for treating a condition in a mammal. This method includes administering to the mammal a pharmaceutically acceptable carrier and an effective amount of a pharmaceutically acceptable composition comprising a compound having the structure of formula (IV):

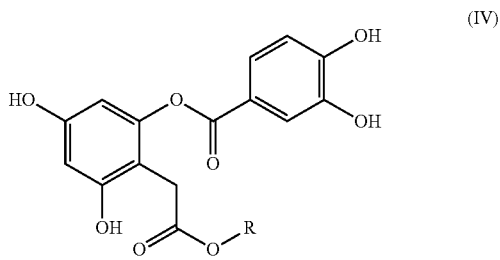

wherein R is selected from H or CH$_3$ or a compound selected from cyanidin 3-glucoside, delphinidin 3-glucoside, or combinations thereof, or an enantiomer, optical isomer, diastereomer, N-oxide, crystalline form, hydrate, or pharmaceutically acceptable salt thereof, and a pharmaceutically acceptable carrier. Preferably, R is CH$_3$.

As used herein, the term "condition" means a symptomatic state or a disease in the mammal. Preferably, the condition is cancer, an inflammatory condition, or both. Preferably, the inflammatory condition is a chronic inflammatory condition. Preferably, the chronic inflammatory condition is rheumatoid arthritis, heart disease, or lung disease. Preferably, the lung disease is COPD. Preferably, the cancer is colon cancer.

In the present invention, an "effective amount" is an amount sufficient to effect beneficial or desired results. An effective amount can be administered in one or more doses. In terms of treatment, an "effective amount" of a depside or anthocyanin for a cell is an amount sufficient to modulate the level of a chemokine in a cell.

In terms of treatment of a mammal, an "effective amount" of the compounds of the present invention (i.e., Compounds 1-4) is an amount sufficient to treat, manage, palliate, ameliorate, or stabilize a condition in the mammal. More particularly, an "effective amount" delivers to the subject from about 1 to about 1000 mg, preferably from about 5 to about 500 mg, more preferably from about 10 to about 250 mg, such as for example, about 20, 40, 60, 80, 100, 120, 140, 160, 180, 200, 220, or 240 mg of one of the compounds of the present invention.

The effective amount is generally determined by a physician on a case-by-case basis and is within the skill of one in the art. Several factors are typically taken into account when determining an appropriate dosage. These factors include age, sex and weight of the patient, the condition being treated, the severity of the condition and the form of the drug being administered. For instance, the amount of a derivative of a compound of formula (I) may not need to be as high as that of the compound of formula (I) itself in order to be therapeutically effective.

Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of animal, and like factors well known in the arts of medicine and veterinary medicine. In general, a suitable dose of one of the compounds according to the invention will be that amount of the compound, which is the lowest dose effective to produce the desired effect. The effective dose of a compound according to the invention maybe administered as two, three, four, five, six or more sub-doses, administered separately at appropriate intervals throughout the day.

A compound of the present invention may be administered in any desired and effective manner: as pharmaceutical compositions for oral ingestion, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. Further, a compound of the invention may be administered in any combination with each other and/or in conjunction with other treatments. A compound of invention maybe encapsulated or otherwise protected against gastric or other secretions, if desired.

In an embodiment of the present invention, the compound or composition of the present invention is formulated for aerosol administration, particularly to the respiratory tract. The compound or composition generally has a small particle size, e.g., about 5 microns or less. Such a particle size may be obtained by means known in the art, for example by micronization. The particles of the compound or composition are provided in a pressurized pack with a suitable propellant such as a chlorofluorocarbon (CFC), for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by a metered valve. Alternatively, the compound or composition may be provided in a form of a dry powder, for example a powder mix of the compound in a suitable powder base such as lactose, starch, starch derivatives such as hydroxypropylmethyl cellulose and polyvinylpyrrolidine (PVP). The powder composition may be presented in unit dose form, for example in capsules or cartridges of, e.g., gelatin or blister packs from which the powder may be administered by means of an inhaler. See, e.g., Berg, Published International Application No. WO 2002/009699; Sedwell, R. W. et al., Chemptherapy, 40(1):43-56 (1994).

While it is possible for a compound of the invention to be administered alone, it is preferable to administer the compound(s) as a pharmaceutical formulation (composition). The pharmaceutically acceptable compositions comprise one or more compounds of the present invention as an active ingredient in admixture with one or more pharmaceutically-acceptable carriers and, optionally, one or more other compounds, drugs, ingredients and/or materials. Regardless of the route of administration selected, the compounds of the present invention are formulated into pharmaceutically-acceptable dosage forms by conventional methods known to those of skill in the art. See, e.g., Remington's Pharmaceutical Sciences (Mack Publishing Co., Easton, Pa.).

Another aspect of this embodiment is a method for killing a cancer cell. In this method, an effective amount of the pharmaceutical composition as defined above is administered. Preferably, the cancer cell is a colon cancer cell. In another aspect of this method, the pharmaceutical composition is conjointly administered with at least one agent.

In the present invention, one or more compounds of the present invention may be conjointly administered to the mammal with an agent that kills cells through, e.g., an apoptotic mechanism. In this aspect, the agent is, e.g., a chemotherapeutic agent—including combinations of chemotherapeutic agents. Agents useful in the present invention include, e.g., an EGF-receptor antagonist, arsenic sulfide, adriamycin, cisplatin, carboplatin, cimetidine, carminomycin, mechlorethamine hydrochloride, pentamethylmelamine, thiotepa, teniposide, cyclophosphamide, chlorambucil, demethoxyhypocrellin A, melphalan, ifosfamide, trofosfamide, Treosulfan, podophyllotoxin or podophyllotoxin derivatives, etoposide phosphate, teniposide, etoposide, leurosidine, leurosine, vindesine, 9-aminocamptothecin, camptoirinotecan, crisnatol, megestrol, methopterin, mitomycin C, ecteinascidin 743, busulfan, carmustine (BCNU), lomustine (CCNU), lovastatin, 1-methyl-4-phenylpyridinium ion, semustine, staurosporine, streptozocin, phthalocyanine, dacarbazine, aminopterin, methotrexate, trimetrexate, thioguanine, mercaptopurine, fludarabine, pentastatin, cladribin, cytarabine (ara C), porfiromycin, 5-fluorouracil, 6-mercaptopurine, doxorubicin hydrochloride, leucovorin, mycophenolic acid, daunorubicin, deferoxamine, floxuridine, doxifluridine, raltitrexed, idarubicin, epirubican, pirarubican, zorubicin, mitoxantrone, bleomycin sulfate, actinomycin D, safracins, saframycins, quinocarcins, discodermolides, vincristine, vinblastine, vinorelbine tartrate, vertoporfin, paclitaxel, tamoxifen, raloxifene, tiazofuran, thioguanine, ribavirin, EICAR, estramustine, estramustine phosphate sodium, flutamide, bicalutamide, buserelin, leuprolide, pteridines, enediynes, levamisole, aflacon, interferon, interleukins, aldesleukin, filgrastim, sargramostim, rituximab, BCG, tretinoin, betamethosone, gemcitabine hydrochloride, verapamil, VP-16, altretamine, thapsigargin, oxaliplatin, iproplatin, tetraplatin, lobaplatin, DCP, PLD-147, JM118, JM216, JM335, satraplatin, docetaxel, deoxygenated paclitaxel, TL-139, 5'-nor-anhydrovinblastine (hereinafter: 5'-nor-vinblastine), camptothecin, irinotecan (Camptosar, CPT-11), topotecan (Hycamptin), BAY 38-3441, 9-nitrocamptothecin (Orethecin, rubitecan), exatecan (DX-8951), lurtotecan (GI-147211C), gimatecan, homocamptothecins diflomotecan (BN-80915) and 9-aminocamptothecin (IDEC-13'), SN-38, ST1481, karanitecin (BNP1350), indolocarbazoles (e.g., NB-506), protoberberines, intoplicines, idenoisoquinolones, benzo-phenazines or NB-506.

Pharmaceutical carriers are well known in the art (see, e.g., Remington's Pharmaceutical Sciences (Mack Publishing Co., Easton, Pa.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringers injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly (anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each carrier used in a pharmaceutical composition of the invention must be "acceptable" in the sense of being compatible with the other ingredients of the formulation and not injurious to the subject. Carriers suitable for a selected dosage form and intended route of administration are well known in the art, and acceptable carriers for a chosen dosage form and method of administration can be determined using ordinary skill in the art.

The pharmaceutically acceptable compositions (or acceptable compositions in the case of, e.g., feed supplements) of the invention may, optionally, contain additional ingredients and/or materials commonly used in pharmaceutical compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monosterate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monosterate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

Pharmaceutical formulations suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared by mixing the active ingredient(s) with one or more pharmaceutically-acceptable carriers and, optionally, one or more fillers, extenders, binders, humectants, disintegrating agents, solution retarding agents, absorption accelerators, wetting agents, absorbents, lubricants, and/or coloring agents. Solid compositions of a similar type maybe employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein. These compositions may also optionally contain opacifying agents and may be of a composition such that they release the active ingredient only, or preferentially, in a certain portion of the gastrointestinal tract, optionally, in a delayed manner. The active ingredient can also be in microencapsulated form.

Liquid dosage forms for oral administration include pharmaceutically-acceptable emulsions, microemulsions, solutions, suspensions, syrups and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

Formulations for rectal or vaginal administration may be presented as a suppository, which maybe prepared by mixing one or more active ingredient(s) with one or more suitable nonirritating carriers which are solid at room temperature, but liquid at body temperature and, therefore, will melt in the rectum or vaginal cavity and release the active compound. Formulations which are suitable for vaginal administration also include pessaries, tampons, creams, gels, pastes, foams or spray formulations containing such pharmaceutically-acceptable carriers as are known in the art to be appropriate.

Dosage forms for the topical or transdermal administration include powders, sprays, ointments, pastes, creams, lotions, gels, solutions, patches, drops and inhalants. The active compound may be mixed under sterile conditions with a suitable pharmaceutically-acceptable carrier. The ointments, pastes, creams and gels may contain excipients. Powders and sprays may contain excipients and propellants.

Pharmaceutical compositions suitable for parenteral administrations comprise one or more compounds of the present invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

In some cases, in order to prolong the effect of a drug, it is desirable to slow its absorption from subcutaneous or intramuscular injection. This may be accomplished by the use of a liquid suspension of crystalline or amorphous material having poor water solubility.

The rate of absorption of the drug then depends upon its rate of dissolution which, in turn, may depend upon crystal size and crystalline form. Alternatively, delayed absorption of a parenterally-administered drug may be accomplished by dissolving or suspending the drug in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

Another embodiment of the present invention is a method for treating or ameliorating chronic obstructive pulmonary disease (COPD). This method includes administering to a mammal an effective amount of a composition comprising a pharmaceutically acceptable carrier and a compound having the structure of formula (IV):

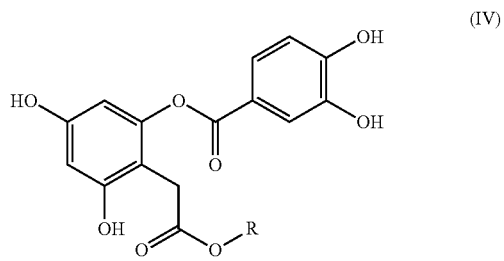

wherein R is selected from H or CH$_3$ or a compound selected from cyanidin 3-glucoside, delphinidin 3-glucoside, or combinations thereof, or an enantiomer, optical isomer, diastereomer, N-oxide, crystalline form, hydrate, or pharmaceutically acceptable salt thereof. In this method, the mammal is preferably a human. It is also preferred that R is $CH_3$.

A further embodiment of the present invention is a unit dosage form comprising a pharmaceutically acceptable carrier and a compound having the structure of formula (IV):

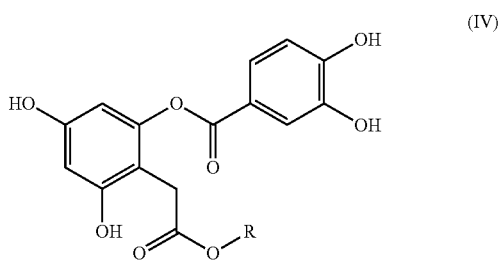

wherein R is selected from H or $CH_3$ or a compound selected from cyanidin 3-glucoside, delphinidin 3-glucoside, or combinations thereof, or an enantiomer, optical isomer, diastereomer, N-oxide, crystalline form, hydrate, or pharmaceutically acceptable salt thereof. In this method, it is preferred that R is $CH_3$.

An additional embodiment of the present invention is a food or feed supplement comprising an acceptable carrier, such as for example, a pharmaceutically acceptable carrier as defined above, and a compound having formula (IV):

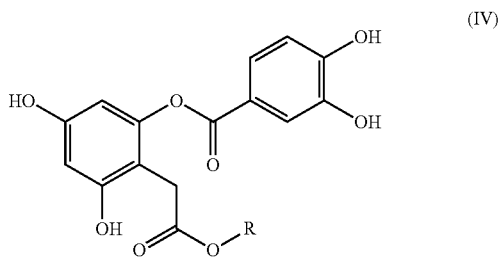

wherein R is selected from H or $CH_3$ or a compound selected from cyanidin 3-glucoside, delphinidin 3-glucoside, or combinations thereof, or an enantiomer, optical isomer, diastereomer, N-oxide, crystalline form, hydrate, or pharmaceutically acceptable salt thereof. In this method, it is preferred that R is $CH_3$.

Another embodiment of the present invention is an extract obtained from the fruit of *Myrciaria cauliflora* comprising, in substantially pure form, a compound having formula (IV):

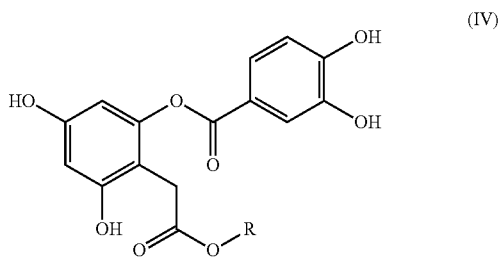

wherein R is selected from H or $CH_3$ or a compound selected from cyanidin 3-glucoside, delphinidin 3-glucoside, or combinations thereof. Preferably, R is $CH_3$.

In the present invention, "substantially pure form" means that the extract contains at least one compound of the present invention that is at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

An aspect of this embodiment is a food or feed supplement (as described above) containing the extract. Another aspect of this embodiment is a pharmaceutical composition containing the extract and a pharmaceutically acceptable carrier, as described above.

Another aspect of this embodiment is a method for treating or ameliorating a condition in a mammal comprising administering to a mammal an effective amount of a composition containing the extract. Preferably, the mammal is a human.

The conditions treated, forms and formulations of the composition, methods of administration and delivery routes for the composition, and effective doses are as defined above.

The following examples are provided to further illustrate the compositions and methods of the present invention. These examples are illustrative only and are not intended to limit the scope of the invention in any way.

EXAMPLES

I. General Experimental Procedures

UV spectra were measured on a Perkin-Elmer Lambda 35 UV/VIS spectrometer. NMR experiments were conducted on a Bruker Avance AV300 NMR spectrometer operating at 300.13 MHz for $^1H$ and 75.48 MHz for $^{13}C$ using standard Bruker software. Mass spectra were obtained on a ThermoFinnigan LCQ utilizing both ESI and APCI in the positive and negative modes. HRESIMS was performed on a Micromass Q-TOF Ultima mass spectrometer. HPLC was done on a Waters 2695 using a Phenomenex Aqua column (250×4.6 mm, 5 µm) and monitored using a Waters 996 PDA scanning from 240 to 600 nm. Column chromatography was accomplished using Sephadex LH-20 (Pharmacia, 25-100 µm), reversed-phase C18 silica gel (J. T. Baker, 40 µm), and Diaion HP-20 (Mitsubishi, Japan). Separations were monitored using silica gel 60 F254 and RP18 F254 TLC plates (1 mm thickness, EM Science, Germany). Quercetin, rutin, cinnamic acid, O-coumaric acid, gallic acid, and 1,1-diphenyl-2-picrylhydrazyl (DPPH) were purchased from Sigma (MO, USA). Isoquercitrin and myricitrin were previously isolated in the laboratory (23).

II. Plant Material

Fruits of *M. cauliflora* were collected at the Fruit and Spice Park in Homestead, Fla., immediately frozen and shipped by overnight courier on dry ice to the laboratory, where they were kept in cold (−20° C.), dark storage until processed. A voucher specimen (Reynertson 39) was prepared, identified, and deposited at the Steere Herbarium of The New York Botanical Garden (Bronx, N.Y.).

III. Extraction and Isolation Procedures

Deseeded fresh fruits (6.2 kg) were homogenized in a blender with MeOH, extracted exhaustively and concentrated in vacuo at temperatures not exceeding 40° C. to give a thick syrup that was diluted with water. The aqueous solution was separated over Diaion HP-20 and eluted using $H_2O$, MeOH, and acetone. The MeOH fraction was concentrated to give a residue (52 g). A portion (44 g) of that residue was subjected to Sephadex LH-20 column chromatography (about 125 g) in amounts of 8, 11, 12, and 13 g and eluted with formic acid:water:MeOH (1:9:10). Fractions from all four columns were recombined to give 8 fractions (A-H). Fractions D (3.74 g) and E (111 mg) were chromatographed over Sephadex LH-20 and eluted using MeOH:formic acid (9:1). The recombined fraction A1 was then separated in a smaller Sephadex LH-20 column (12 g) using an isocratic system of acetonitrile-water. Fractions A1$_{35-59}$ were recombined as fraction A2 and subjected to reversed-phase C18 column chromatography (6 g) using 10% formic acid:acetonitrile (95:5 to 50:50; 5% gradient; 20 ml each eluant, fractions of 3 mL). Fractions A2$_{12-27}$ were recombined and subjected to final purification using Sephadex LH-20 and water-acetonitrile to give 16 mg of Compound 1. Compound 2 was isolated according to an analogous scheme to give 10 mg.

Approximately 50 g of freeze-dried fruits were extracted in EtOH and subjected to LC-MS selected ion monitoring (SIM) analysis to determine if Compound 1 was a methyl ester artifact of Compound 2 following extraction in MeOH. Analysis was performed in negative ESI mode, using a gradient of 0.1% formic acid (A) and acetonitrile (B) from 95% A to 50% A over 30 minutes, monitoring [M-H]$^-$ m/z 332 to 334. A [M-H]$^-$ molecular ion m/z=333 with the same retention time as Compound 1 was detected in ethanolic extracts, indicating that Compound 1 is produced by the plant itself.

A. Jaboticabin (methyl 2-[(3,4-dihydroxybenzoyloxy)-4,6-dlhydroxyphenyl]acetate)

From reference: Compound 1 is a reddish amorphous solid (MeOH); UV (MeOH) $\lambda_{max}$ (log ε) 267.5 (3.35), 298.5 (3.16) nm; $^1$H NMR (CD$_3$OD, 300.13 MHz) δ 7.55 (1H, dd, J=2.1, 7.8 Hz, H-6'), 7.54 (1H, d, J=2.1 Hz, H-2'), 6.88 (1H, d, J=7.8 Hz, H-5'), 6.27 (1H, d, J=2.4 Hz, H-5), 6.16 (1H, d, J=2.4 Hz, H-3), 3.57 (3H, s, OCH$_3$-8), 3.50 (2H, s, H-7); $^{13}$C NMR (CD$_3$OD, 75.48 MHz) δ 172.9 (C, C-8), 164.9 (C, C-7'), 166.4 (C-2'), 157.2 (C, C-4), 157.0 (C, C-2), 151.1 (C, C-6), 145.0 (C, C-3'), 122.9 (CH, C-6'), 120.3 (C, C-1'), 114.7 (CH, C-5'), 105.7 (C, C-1), 100.7 (CH, C-5), 99.6 (CH, C-3), 50.9 (OCH$_3$-8), 28.5 (CH$_2$, C-7); ESIMS m/z 333 [M-H]$^-$ (C$_{16}$H$_{14}$O$_8$), HRESIMS m/z 357.0581 [M+Na]$^+$ (calculated for C$_{16}$H$_{14}$O$_8$Na, 357.0586).

Compound 1 was isolated as a reddish amorphous powder. The negative ESI mass spectrum showed a [M-H]$^-$ molecular ion of m/z=333. Positive HRESIMS gave a [M+Na]$^+$ molecular ion of m/z=357.0581, corresponding to a molecular formula of C$_{16}$H$_{14}$O$_8$. The UV spectrum exhibited a peak at 267 nm with a shoulder at 298 nm, typical of a phenolic acid ester. The $^1$H- and $^{13}$C-NMR experiments were similar to literature values for Compound 2 with the addition of a methoxy signal at δ 3.57 (3H, s, OCH$_3$-8) and 50.9 (OCH$_3$-8) (11). The position of the methoxy group was established through HMBC correlations between the proton signal at δ 3.57 (OCH$_3$-8) and δ 172.9 (C-8). The C-1 attachment for the methyl acetate group followed from HMBC correlations; the methylene proton signal at δ 3.50 (H-7) showed HMBC correlations with C-1, C-2, C-6, and the carbonyl C-8. A detailed analysis of 1-D and 2-D NMR spectra and comparison with Compound 2 confirmed the structure of jaboticabin (Compound 1) as methyl 2-[(3,4-dihydroxybenzoyloxy)-4,6-dihydroxyphenyl]acetate:

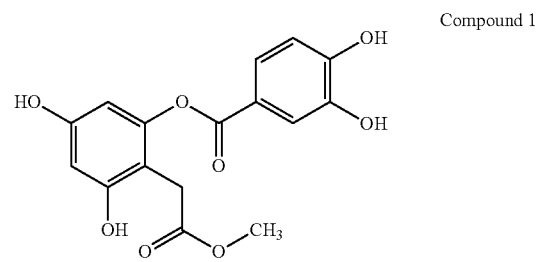 [SMILES: COC(=O)Cc1c(O)cc(O)cc1OC(=O)c1ccc(O)c(O)c1]
Compound 1

An ethanolic extract of *jaboticaba* fruits was analyzed by LC-MS in SIM mode to determine if Compound 1 was a methyl ester artifact from the initial MeOH extraction. A [M-H]$^-$ molecular ion m/z=333 with the same retention time as Compound 1 was detected in ethanolic extracts, further confirming that Compound 1 is produced by the plant itself.

B. Other Isolated Compounds

Compounds 2, 3, 4, pyranocyanin B, protocatechuic acid, methyl protocatechuate, ellagic acid, quercimeritrin, and quercitrin were isolated and identified by comparison of spectroscopic measurements to published literature values (11, 15). Quercetin, isoquercitrin, rutin, myricitrin, cinnamic acid, O-coumaric acid, and gallic acid were identified by comparison of retention time, UV, and MS data to authentic standards.

IV. 1,1-Diphenyl-2-plcrylhydrazyl (DPPH) Assay

The DPPH assay was performed on extracts, fractions, and purified compounds as previously described, using 400 μM DPPH (9). Gallic acid was used as a positive control (IC$_{50}$=30.0±2.9 μM). The results are reported in Table 1:

TABLE 1

| DPPH assay results. | |
|---|---|
| Compound | DPPH Assay IC$_{50}$ (μM) |
| Compound 1 | 51.4 |
| Compound 2 | 61.8 |
| Compound 3 | 28.4 |
| Compound 4 | 26.3 |
| Gallic acid (Control) | 30.0 |

The DPPH assay is an indication of the ability of a substance to scavenge free radicals. Gallic acid is know to be an effective free radical scavenger. Accordingly, the results in Table 1 demonstrate that Compounds 1-4 exhibit good antiradical activity.

V. IL-8 Immunoassay

Human SAE cells were cultured according to supplier instructions (Clonetics, CA) and maintained in a controlled atmosphere of air-5% CO$_2$ at 37° C. Confluent SAE cells at passages 4-8 were used for experiments.

Cigarette smoke extract (CSE) was prepared using a modified protocol (24). Briefly, a Barnet vacuum pump operating at constant flow was used to draw the smoke of one unfiltered 2R1 reference cigarette (University of Kentucky) through 25 mL of Dulbecco's phosphate-buffered saline. This solution (100% CSE) was adjusted to pH 7.4, filtered, diluted with small airway growth medium to a final concentration of 5%, and added to the cells immediately.

Cells were treated with 5% CSE or pure compounds (100 μM), or pretreated with pure compounds 30 minutes prior to 5% CSE exposure. After 24 hours measurement of human IL-8 in cell culture supernates was performed by ELISA (R&D Systems Inc., MN). Statistical analyses were performed by Student's t-test (two-sided) using the JMP Statistics software package (SAS Institute Inc., NC) and defined at the 5% level. The results are reported in Table 2:

TABLE 2

IL-8 immunoassay results.

| Compound | IL-8 inhibition in SAE cells | |
|---|---|---|
| | Untreated | Treated with 5% CSE |
| Compound 1 | 81.3% | 47.3% |
| Compound 2 | 74.9% | 70.3% |
| Compound 3 | 65.3% | 36.4% |
| Compound 4 | Not Detected | 96.0% |
| Catechin | No Change | 60.3% |

As shown in Table 2, Compound 1 decreases IL-8 production in untreated SAE cells by 81.3% and decreases IL-8 production in SAE cells treated with 5% CSE by 47.3%. Compound 2 inhibits IL-8 production by 74.9% in untreated SAE cells and 70.3% in treated SAE cells.

IL-8 is not detected in SAE cells treated with Compound 4. Compound 4 causes a 96% reduction in IL-8 production in SAE cells treated with CSE. Compound 3 inhibits IL-8 production by 65.3% (untreated) and 36.4% (treated), respectively.

VI. Cytotoxicity Assays

Colon cancer cell lines HT29, HCT116, and SW480 (10,000 cells) were plated into 24-well plates in Dulbecco's modified Eagle medium (DMEM) containing 10% fetal bovine serum (FBS). After 24 hours, cells were treated with 6 concentrations (1, 5, 10, 30, 50, and 70 μM) of Compounds 1-4 and 5-fluorouracil (5-FU) and incubated for 72 hours under DMEM containing 1% FBS. The plates were washed with PBS once and the attached cells were collected by tripsinization. The numbers of cells were counted using a Coulter Counter (Beckman Coulter Co., CA) as previously described (25). The results are reported in Table 3:

TABLE 3

Cytotoxicity assays results.

| Compound | $IC_{50}$ (μM) | | |
|---|---|---|---|
| | HT29 | HCT116 | SW480 |
| Compound 1 | 65 | >100 | not tested |
| Compound 2 | >100 | 30 | not tested |
| Compound 3 | ~100 | ~70 | ~90-100 |
| Compound 4 | ~100 | 12 | 20 |
| 5-FU | 46.1 | 45.1 | 53.0 |

The cytotoxicity of Compounds 1, 2, and 4 is comparable to $IC_{50}$ values for 5-FU, a drug used for colon cancer treatment and to the positive controls epigallocatechin gallate (EGCG) and Polyphenon E (Poly E), a standardized decaffeinated green tea extract (8, 19). EGCG and Poly E exhibited HT29 $IC_{50}$ of 27 μg/mL and 22 μg/mL, respectively. Compound 1 is cytotoxic against HT29 colon cancer cells ($IC_{50}$=65 μM). Compound 2 is cytotoxic against HCT116 colon cancer cells ($IC_{50}$=30 μM). Consistent with published literature, Compound 4 was more cytotoxic than Compound 3 (20). Compound 4 showed good activity against both the HCT116 and SW480 cell lines ($IC_{50}$=12 and 20 μM, respectively), while Compound 3 inhibited 50% cell growth only at the 100 μM range.

CITED DOCUMENTS

The following documents, cited above, are incorporated by reference as if recited in full herein:

(1) Morton, J. *Fruits of Warm Climates*. Julia Morton: Winterville, N.C., 1987; pp 386-388.
(2) Popenoe, W. *Manual of Tropical and Subtropical Fruits*. Hafner Press: New York, 1920; pp 272-311.
(3) Giacometti, D.; Lleras, E. In *Neglected Crops: 1492 from a Different Perspective*; Bermejo, J. E. H.; León, J., Eds.; FAO: Rome, 1994; pp 229-237.
(4) Einbond, L. S.; Reynertson, K. A.; Luo, X.-D.; Basile, M. J.; Kennelly, E. J. *Food Chem.* 2004, 84, 23-28.
(5) Trevisan, L. M.; Bobbio, F. O.; Bobbio, P. A. *J. Food Sci.* 1972, 37, 818-819.
(6) Zanatta, C. F.; Cuevas, E.; Bobbio, F. O.; Winterhalter, P.; Mercadante, A. *J. Agric. Food Chem.* 2005, 53, 9531-9535.
(7) Baggett, S.; Protiva, P.; Mazzola, E. P.; Yang, H.; Ressler, E. T.; Basile, M. J.; Weinstein, I. B.; Kennelly, E. J. *J. Nat. Prod.* 2005, 68, 354-360; (b) Ma, J.; Luo, X.-D.; Protiva, P.; Yang, H.; Ma, C.; Basile, M. J.; Weinstein, I. B.; Kennelly, E. J. *J. Nat. Prod.* 2003, 66, 983-986.
(8) Yang, H.; Protiva, P.; Gil, R. R.; Jiang, B.; Baggett, S.; Basile, M. J.; Reynertson, K. A.; Weinstein, I. B.; Kennelly, E. J. *Planta Med.* 2005, 71, 852-860.
(9) Yang, H.; Protiva, P.; Cui, B.; Ma, C.; Baggett, S.; Hequet, V.; Mori, S.; Weinstein, I. B.; Kennelly, E. J. *J. Nat. Prod.* 2003, 66, 1501-1504.
(10) Ono, M.; Masuoka, C.; Koto, M.; Tateishi, M.; Komatsu, H.; Kobayashi, H.; Igoshi, K.; Ito, Y.; Okawa, M.; Nohara, T. *Chem. Pharm. Bull.* 2002, 50, 1416-1417; (b) Zgorka, G.; Gowniak, K. *J. Pharm. Biomed. Anal.* 2001, 26, 79-87.
(11) Hillenbrand, M.; Zapp, J.; Becker, H. *Planta Med.* 2004, 70, 378-380.
(12) Kumar K C, S.; Muller, K. *J. Nat. Prod.* 1999, 62, 821-823.
(13) Neamati, N.; Hong, H.; Mazumder, A.; Wang, S.; Sunder, S.; Nicklaus, M. C.; Milne, G. W. A.; Proksa, B.; Pommier, Y. *J. Med. Chem.* 1997, 40, 942-951; (b) Nielsen, J.; Nielsen, P. H.; Frisvad, J. C. *Phytochemistry.* 1998, 50, 263-265.
(14) Gerrard, J. M.; Peterson, D. A. *Prostaglandins Leukot. Med.* 1984, 13, 139-142; (b) Sankawa, U.; Shibuya, M.; Ebizuka, Y.; Noguchi, H.; Kinoshita, T.; Iitaka, Y. *Prostaglandins.* 1982, 24, 21-33; (c) Kumar K C, S.; Muller, K. *J. Nat. Prod.* 1999, 62, 817-820; (d) Kumar K C, S.; Muller, K. *Eur. J. Med. Chem.* 2000, 35, 405-411.
(15) Agrawal, P. K.; Bansal M. C. In *Carbon-13 NMR of Flavonoids*; Agrawal, P. K., Ed.; Elsevier: New York, 1989; Vol. 39, pp 283-364; (b) Yu, Y.; Sun, Y.; Foo, L. Y. *Tetrahedron Lett.* 2000, 41, 5975-5978; (c) Seeram, N. P.; Lee, R.; Scheuller, H. S.; Heber, D. *Food Chem.* 2006, 97, 1-11; (d) Ikuta, H.; Fukai, T.; Nomura, T.; Uzawa, J. *Heterocycles.* 1985, 23, 121-126; (e) Miyazawa, M.; Oshima, T.; Koshio, K.; Itsuzaki, Y.; Anzai, J. *J. Agric. Food Chem.* 2003, 51, 6953-6956; (f) Sang, S.; Lapsley, K.; Jeong, W.-S.; Lachance, P. A.; Ho, C.-T.; Rosen, R. T. *J. Agric. Food Chem.* 2002, 50, 2459-2463.

(16) de Boer, W. I. Chest. 2002, 121, 209S-218S; (b) Barnes, P. J. Potential novel therapies for chronic obstructive pulmonary disease, In *Chronic Obstructive Pulmonary Disease: Pathogenesis to Treatment*, Wiley & Sons: 2001; pp 255-272.

(17) Koefler, S.; Nickel, T.; Weis, M. *Clin. Sci.* 2005, 108, 205-213.

(18) Biswas, S. K.; McClure, D.; Jimenez, L. A.; Megson, I. L.; Rahman, I. *Antioxid. Redox Signal.* 2005, 7, 32-41.

(19) Shimizu, M.; Deguchi, A.; Lim, J. T. E.; Moriwaki, H.; Kopelovich, L.; Weinstein, I. B. *Clin. Cancer Res.* 2005, 11, 2735-2745.

(20) Marko, D.; Puppel, N.; Tjaden, Z.; Jakobs, S.; Pahlke, G. *Mol. Nutr. & Food Res.* 2004, 48, 318-325; (b) Meiers, S.; Kemeny, M.; Weyland, U.; Gastpar, R.; Angerer, E. v.; Marko, D. *J. Agric. Food Chem.* 2001, 49, 958-962.

(21) Kong, J.-M.; Chia, L.-S.; Goh, N.-K.; Chia, T.-F.; Brouillard, R. *Phytochemistry.* 2003, 64, 923-933.

(22) Cimino, F.; Ambra, R.; Cana, R.; Saija, A.; Virgili, F. *J. Agric. Food Chem.* 2006, 54, 4041-4047.

(23) Luo, X.-D.; Basile, M. J.; Kennelly, E. J. *J. Agric. Food Chem.* 2002, 50, 1379-1382.

(24) Laurent, P.; Janoff, A.; Kagan, H. M. *Am. Rev. Respir. Dis.* 1983, 127, 189-192.

(25) Shimizu, M.; Suzui, M.; Deguchi, A.; Lim, J. T. E.; Weinstein, I. B. *Clin. Can. Res.* 2004, 10, 1130-1140.

The scope of the present invention is not limited by the description, examples, and suggested uses herein and modifications can be made without departing from the spirit of the invention. Thus, it is intended that the present invention cover modifications and variations of this invention provided that they come within the scope of the appended claims and their equivalents.

What is claimed is:

1. A method for treating or ameliorating chronic obstructive pulmonary disease (COPD) comprising: administering to a mammal an effective amount of a composition comprising a pharmaceutically acceptable carrier and a compound having the structure of formula (IV):

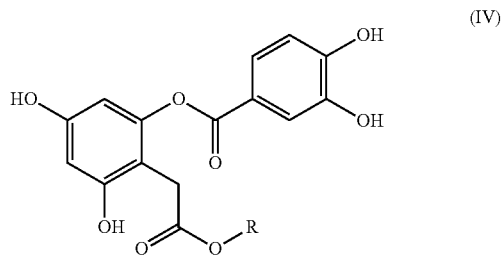

wherein R is selected from H or CH$_3$ or an enantiomer, optical isomer, diastereomer, N-oxide, crystalline form, hydrate, or pharmaceutically acceptable salt thereof.

2. The method according to claim 1, wherein the mammal is a human.

3. The method according to claim 1, wherein R is CH$_3$.

4. A method for treating or ameliorating chronic obstructive pulmonary disease (COPD) in a mammal comprising administering to a mammal an effective amount of a composition comprising an extract obtained from the fruit of *Myrciaria cauliflora* comprising, in substantially pure form, a compound having formula (IV):

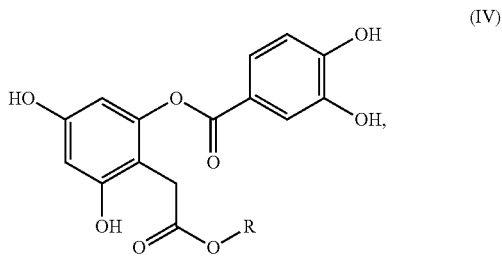

wherein R is selected from H or CH$_3$.

5. The method according to claim 4, wherein the mammal is a human.

6. The method according to claim 4, wherein the effective amount is from about 1 to about 1000 mg.

7. The method according to claim 6, wherein the effective amount is from about 10 to about 250.

* * * * *